United States Patent [19]

Lombardo et al.

[11] Patent Number: 4,895,861

[45] Date of Patent: Jan. 23, 1990

[54] NOVEL NAPHTHALENYL-3H-1,2,3,5-OXA-THIADIAZOLE 2-OXIDES USEFUL AS ANTIHYPERGLYCEMIC AGENTS

[75] Inventors: Louis J. Lombardo, South Plainfield; Thomas R. Alessi, Monmouth Junction, both of N.J.

[73] Assignee: American Home Products Corporation, New York, N.Y.

[21] Appl. No.: 341,609

[22] Filed: Apr. 21, 1989

[51] Int. Cl.$^4$ .................... C07D 291/04; A61K 31/41
[52] U.S. Cl. ..................................... 514/360; 548/122
[58] Field of Search ........................ 514/360; 548/122

[56] References Cited

U.S. PATENT DOCUMENTS 4,148,801  4/1979  Santilli ................................. 564/224

OTHER PUBLICATIONS

Eloy Bull Soc. Chem Belg. 74 129 (1965).
A. Dondoni et al., J. Org. Chem., 42 (21), 3372–3377 (1977).
A. Y. Chang et al., Diabetes, 32, 830–838 (1983).

*Primary Examiner*—Robert Gerstl
*Attorney, Agent, or Firm*—Walter Patton

[57] ABSTRACT

This invention relates to novel substituted 3H-1,2,3,5-oxathiadiazole 2-oxides, processes for their preparation, to methods for using the compounds, and to pharmaceutical preparations thereof. The compounds have pharmaceutical properties which render them beneficial for the treatment of diabetes mellitus and associated conditions.

16 Claims, No Drawings

NOVEL NAPHTHALENYL-3H-1,2,3,5-OXATHIADIAZOLE 2-OXIDES USEFUL AS ANTIHYPERGLYCEMIC AGENTS

BACKGROUND OF THE INVENTION

This invention relates to novel (substituted naphthalenyl)-3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

The serious complications of diabetes mellitus such as nephropathy retinopathy, neuropathy and cataract are all associated with an excessive amount of blood glucose. The major therapeutic objective is therefore the normalization of blood glucose, both in the fasting and postprandial situations.

The therapeutic approaches to the treatment of Non-Insulin Dependent Diabetes Mellitus (NIDDM, Type II) involve the use of diet, insulin or orally active hypoglycemic agents. Presently, such orally active hypoglycemic agents are chosen (a) from sulfonylureas such as chloropropamide, glyburide and others or (b) biguanides such as metformin and related products. Both these groups of agents have serious disadvantages. Sulfonylureas, upon chronic use, lose their effectiveness. In contrast, biguanides suffer from serious side effect, lacticacidosis.

More recently, oxazolidinedione (U.S. Pat. No. 4,342,771) and thiazolidinedione (European patent application No. 117,035) derivatives have been described as useful hypoglycemic agents. U.S. Pat. No. 4,461,902 discloses substituted 5-[(4-cyclohexyl-methoxyphenyl)-methyl]thiazolidine-2,4-diones of formula

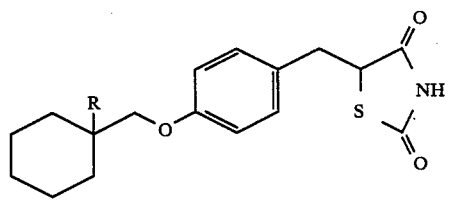

wherein R is methyl (ciglitazone) and related analogues as hypoglycemic agents.

The compounds of the present invention are represented by formula (I)

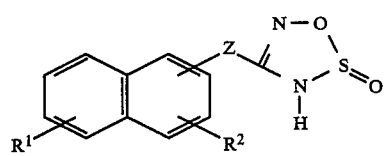

wherein $R^1$ and $R^2$ are independently hydrogen, lower alkyl containing 1 to 6 carbon atoms, alkoxy containing 1 to 6 carbon atoms, ethynyl, methylthio, nitro or halogen; Z is

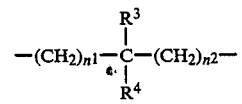

wherein $R^3$ is hydrogen, lower alkyl containing 1 to 3 carbon atoms, alkoxy containing 1 to 2 carbon atoms, or benzyl; $R^4$ is lower alkyl containing 1 to 3 carbon atoms, alkoxy containing 1 to 2 carbon atoms, or benzyl; $n^1$ is 0, 1, or 2; $n^2$ is 0, 1, or 2; or Z is —S—CH$_2$—, —SO$_2$—CH$_2$— or —OCH$_2$—; or Z is —C($R^5$)=C($R^6$)—, wherein $R^5$ and $R^6$ are independently hydrogen or lower alkyl containing 1 to 3 carbon atoms, and the pharmaceutically acceptable salts thereof.

Preferred compounds of the present invention are represented by formula (II)

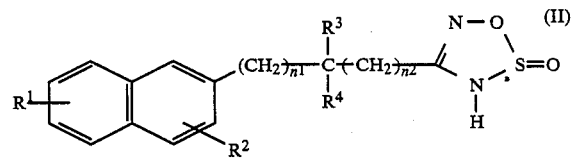

wherein $R^1$ and $R^2$ are independently hydrogen, lower alkyl containing 1 to 6 carbon atoms, or halogen; $n^1$ and $n^2$ are independently 0 or 1; $R^3$ is hydrogen, lower alkyl containing 1 to 3 carbon atoms, alkoxy containing 1 to 2 carbon atoms; $R^4$ is lower alkyl containing 1 to 3 carbon atoms or alkoxy containing 1 to 2 carbon atoms, and the pharmaceutically acceptable salts thereof.

The oxathiadiazole 2-oxide portion of the compounds of the present invention can exist in more than one tautomeric form. For clarity, only one of the tautomers is represented in the generic formulas (I) and (II) above. The possible tautomeric forms are listed below:

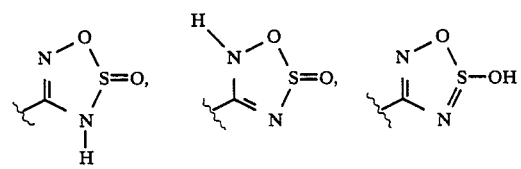

All of said tautomers are included in the present invention. The actual tautomeric form which the compounds of the present invention assume is not known.

This invention also includes mixtures of optically active isomers or partially or completely resolved isomers of the compounds disclosed.

The compounds of this invention are useful as antidiabetic agents for the reduction of blood/plasma sugar levels and for the treatment and/or prevention of diabetic complications and as antihyperlipidemic and antihyperinsulinemic agents.

The still further preferred compounds of the present invention are:
4-[1-(5-bromo-2-naphthalenyl)ethyl]-3H-1,2,3,5-oxathiadiazole 2-oxide;
4-[1-(3-methyl-2-naphthalenyl)ethyl]-3H-1,2,3,5-oxathiadiazole 2-oxide;
4-[1-methyl-2-(2-naphthalenyl)ethyl]-3H-1,2,3,5-oxathiadiazole 2-oxide;
4-[1-(2-naphthalenyl)ethyl]-3H-1,2,3,5-oxathiadiazole 2-oxide;

4-[(2-naphthalenyloxy)methyl]-3H-1,2,3,5-oxathiadiazole 2-oxides;

4-[2-(2-naphthalenyl)ethyl]-3H-1,2,3,5-oxathiadiazole 2-oxide;

4-[(2-naphthalenylthio)methyl]-3H-1,2,3,5-oxathiadiazole 2-oxide;

4-[2-(2-naphthalenyl)propyl]-3H-1,2,3,5-oxathiadiazole 2-oxide;

4-[1-methyl-1-(2-naphthalenyl)ethyl]-3H-1,2,3,5-oxathiadiazole 2-oxide;

4-[1-(2-naphthalenyl)-2-phenylethyl]-3H-1,2,3,5-oxathiadiazole 2-oxide;

4-[2-methoxy-2-(2-naphthalenyl)ethyl]-3H-1,2,3,5-oxathiadiazole 2oxide;

4-[(2-naphthalenylsulfonyl)methyl]-3H-1,2,3,5-oxathiadiazole 2-oxide;

and the pharmaceutically acceptable salts thereof.

DETAILED DESCRIPTION OF THE INVENTION

The naphthalenyl-3H-1,2,3,5-oxathiadiazole 2-oxides of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredient of this invention is not to be construed as limited to a particular mode of administration. For example, the compounds may be administered orally in solid form containing such excipients as starch, milk, sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the naphthalenyl-3H-1,2,3,5-oxathiadiazole 2-oxides will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects.

For oral administration (or as a suppository) to an adult patient, a preferred level of dosage ranges from about 0.01 to 50 mg/kg body weight/day. For parenteral administration to an adult patient, a preferred level of dosage ranges from about 0.005 to 10 mg/kg body weight/day, once daily or divided into 2 to 4 times a week.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The naphthalenyl-3H-1,2,3,5-oxathiadiazole 2-oxides can also be used in combination with dietary restriction, insulin, sulfonylureas, such as chloropropamide and glyburide, biguanides, such as metformin, aldose reductase inhibitors or hypolipidemic agents to produce a beneficial effect in the treatment of diabetes mellitus. In this instance, commercially available insulin preparations or agents exemplified above are suitable. The compounds hereof can be administered sequentially or simultaneously with insulin or the above exemplified agents. Suitable methods of administration, compositions and doses of the insulin preparations or the above exemplified agents are described in medical textbooks; for instance, "Physicians' Desk Reference", 36 ed., Medical Economics Co., Oradell, N.J., U.S.A., 1982.

GENERAL PROCEDURES FOR THE PRODUCTION OF THE COMPOUNDS OF THE PRESENT INVENTION

All the amidoxime intermediates required for the production of the compounds of the present invention were prepared using one of the two modifications of the procedure shown below:

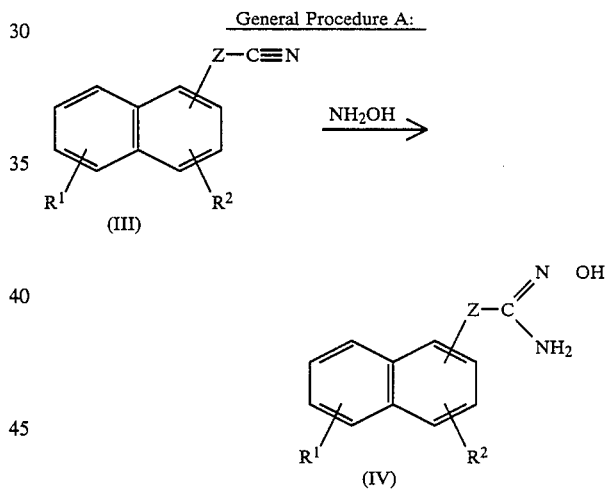

Modification A': NaOEt/EtOH-NaOEt generated by the addition of sodium (1.5 equivalent) to EtOH at room temperature over 30 minutes. This is followed by addition of $NH_2OH \cdot HCl$ (1.5 equivalent) and further stirring for 30 minutes.

Modification A'': NaOMe/MeOH-NaOMe (1.5 equivalent) added to a solution of $NH_2OH \cdot HCl$ (1.5 equivalent) in MeOH at room temperature. This is followed by stirring for 10 minutes.

To an alcoholic solution of $NH_2OH$ free base generated by one of the above methods was added the appropriate nitrile (1.0 equivalent) in alcohol solution. The resulting reaction mixture was stirred for the indicated time period at the indicated temperature after which the alcoholic solvent was removed in vacuo. The residue was either partitioned with water and $CH_2Cl_2$ using standard extractive work-up procedures or stirred with $H_2O$ and filtered and dried in vacuo. The crude amidoximes were either used as such or purified by flash chromatography or trituration with the indicated solvents.

The oxathiadiazole-2-oxides of the present invention were prepared by the general procedure B:

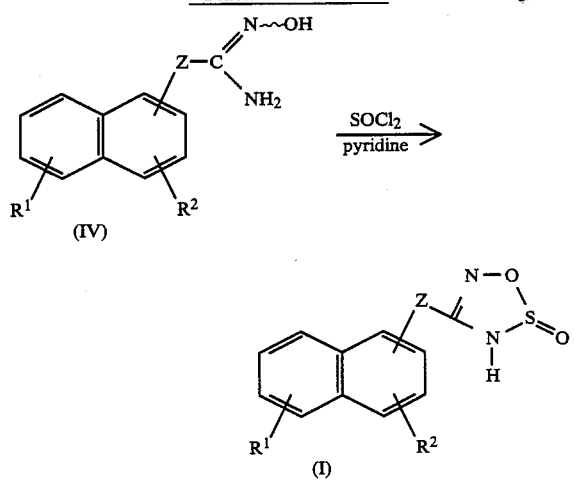

General Procedure B:

To a stirred solution (or suspension) of amidoxime (1 equivalent) and pyridine (2.2 equivalents) in dry CH$_2$Cl$_2$ (1M concentration) cooled to 0° C. was added SOCl$_2$ solution in CH$_2$Cl$_2$ (1.1 equivalent) dropwise over 5 to 10 minutes. The resulting solutions/suspensions were stirred for 30 minutes at 0° C. and poured into H$_2$O. The layers were separated and the aqueous phase was extracted with CH$_2$Cl$_2$ (1x). The combined organic layers were washed with H$_2$O (1x), dried (Na$_2$SO$_4$) and concentrated in vacuo. The crude reaction mixtures were purified by column chromatography or trituration using the indicated solvents to afford analytically pure material in the yield shown for each compound.

EXAMPLE 1

4-[1-(5-Bromo-2-naphthalenyl)ethyl]-3H-1,2,3,5-oxathiadiazole 2-Oxide (Step 1) Preparation of 5-Bromo-2-hydroxymethylnaphthalene To a stirred solution of 5-bromonaphthalene-2-carboxylic acid (10.04 g, 40 mmol) in dry THF (400 mL) cooled to 0° C. was added BH$_3$·THF (54 mL, 54 mmol; 1.0M solution in THF) dropwise over 45 minutes. The resulting solution was stirred overnight while warming to room temperature. The excess BH$_3$ was quenched by the addition of H$_2$O (200 mL) at 0° C. and the volatiles were removed in vacuo. The aqueous residue was extracted with Et$_2$O (2×250 mL) and the combined organic layers were dried (MgSO$_4$) and concentrated in vacuo to give the title compound as a colorless liquid which solidified to a white solid upon standing (9.48 g, 100%). This material was of adequate purity to be used as such in the next step.

NMR (200 MHz, CDCl$_3$): δ 8.10 (d, 1H, J=8 Hz), 7.70 (m, 3H), 7.45 (dd, 1H, J=8,2 Hz), 7.25 (t, 7H, J=8 Hz), 4.75 (s, 2H), 2.55 (br s, 1H).

(Step 2) Preparation of 5-Bromo-2-bromomethylnaphthalene

To a stirred suspension of 5-bromo-2-hydroxymethylnaphthalene (7.00 g, 29.5 mmol) in dry Et$_2$O (100 mL) at 0° C. was added PBr$_3$ (8.91 g, 33 mmol) in portions over 20 minutes. The reaction was stirred for an additional 30 minutes at 0° C., diluted with Et$_2$O (100 mL) and quenched with H$_2$O (100 mL) over 20 minutes. The heterogeneous solution was diluted further with H$_2$O (100 mL) and the layers separated. The aqueous phase was extracted with Et$_2$O (1×200 mL) and the combined organic layers were washed with H$_2$O (1×100 mL) and saturated NaCl (1×100 mL), dried (MgSO$_4$) and concentrated in vacuo. The residue was purified by preparative HPLC (SiO$_2$: gradient hexane/EtOAc) to give the title compound as a white solid (4.60 g, 52%).

NMR (200 MHz, CDCl$_3$): δ 8.40 (d, 1H, J=8 Hz), 7.80 (m, 3H), 7.60 (d, 1H, J=8 Hz), 7.30 (m, 1H), 4.60 (s, 2H).

(Step 3) Preparation of (5-Bromo-2-naphthalenyl)acetonitrile

A suspension of 5-bromo-2-bromomethylnaphthalene (4.50 g, 15 mmol) and NaCN (784 mg, 16 mmol) in 9:1 CH$_3$CN/H$_2$O (150 mL) was heated to reflux for 1 hour during which time the reaction mixture became homogeneous. The solution was cooled to room temperature and the volatiles removed in vacuo. The aqueous residue was partitioned between H$_2$O (200 mL) and CH$_2$Cl$_2$ (200 mL). The aqueous phase was further washed with CH$_2$Cl$_2$ (1×200 mL) and the combined organic layers dried (Na$_2$SO$_4$) and concentrated in vacuo to give the product as a white solid (3.66 g, 99%). This material was of sufficient purity to be used as such without purification.

NMR (300 MHz, CDCl$_3$): δ 8.28 (d, 1H, J=8 Hz), 7.82 (m, 3H), 7.50 (d, 1H, J=8 Hz), 7.38 (t, 1H, J=8 Hz), 3.98 (s, 2H).

(Step 4) Preparation of 2-(5-Bromo-2-naphthalenyl)propionitrile

To a solution of LDA [lithium diisopropylamine prepared from diisopropylamine (1.49 g, 14.8 mmol) and n-BuLi (9.25 mL, 14.8 mmol, 1.6M solution in hexanes)] in THF (80 mL) at −78° C. was added (5-bromo-2-naphthalenyl) acetonitrile (3.80 g, 13.4 mmol) in THF (70 mL) dropwise over 45 minutes. The resulting orange solution was stirred at −78° C. for 10 minutes and MeI (1.90 g, 13.4 mmol) was added in one portion. The reaction mixture was stirred at −78° C. for 1 hour and quenched with saturated NH$_4$Cl (20 mL). The solution was warmed to room temperature and the volatiles removed in vacuo. The residue was diluted with H$_2$O (100 mL) and extracted with Et$_2$O (3×150 mL). The combined organic layers were dried (MgSO)$_4$) and concentrated in vacuo to give the crude product as a yellow oil. This residue was purified by flash chromatography (SiO$_2$) with elution by hexane/CH$_2$Cl$_2$ (2:1), followed by hexane/CH$_2$Cl$_2$ (3:2) to give the title compound as a colorless oil (2.74 g, 79%).

NMR (300 MHz, CDCl$_3$): δ 8.28 (d, 1H, J=8 Hz), 7.82 (m, 3H), 7.52 (d, 1H, J=8 Hz), 7.38 (t, 1H, J=8 Hz), 4.10 (q, 1H, J=7 Hz), 1.73 (d, 3H, J=7 Hz).

(Step 5) Preparation of N′-Hydroxy-2-(5-bromo-2-naphthalenyl)propanimidamide

According to General Procedure A, 2-(5-bromo-2-naphthalenyl)propionitrile 2.73 g, 10 mmol) was refluxed for three days to obtain the product (3.08 g, 100%) as a light green oil which was used as such in the next step.

NMR (300 MHz, CDCl$_3$): δ 8.20 (d, 1H, J=8 Hz), 7.78 (m, 3H), 7.56 (d, 1H, J=8 Hz), 7.30 (t, 1H, J=8 Hz), 4.40 (br s, 2H), 3.81 (q, 1H, J=7 Hz), 1.56 (d, 3H, J=7 Hz).

(Step 6) Preparation of
4-[1-(5-Bromo-2-naphthalenyl)ethyl]-3H-1,2,3,5-oxathiadiazole 2-Oxide N'-Hydroxy-2-(5-bromo-2-naphthalenyl)-propanimidamide (3.08 g, 10 mmol) was converted to the desired product according to General Procedure B. Purification was accomplished by flash chromatography on SiO$_2$ with CH$_2$Cl$_2$ eluent to give the product as a colorless glassy (2.5 g, 70%).

NMR (400 MHz, DMSO-d$_6$):1:1 mixture of diastereomers δ22.44 (s, 1H), 8.13 (d, 0.5H, J=8 Hz), 8.12 (d, 0.5H, J=8 Hz), 7.97 (d, 0.5H, J=8 Hz), 7.95 (d, 0.5H, J=8 Hz), 7.93 (d, 0.5H, J=2 Hz), 7.92 (d, 0.5H, J=2 Hz), 7.88 (s, 0.5H), 7.86 (s, 0.5H), 7.62 (app. t, 1H, J=8 Hz), 7.45 (app. t, 1H, J=8 Hz), 4.44 (q, 0.5H, J=7 Hz), 4.39 (q, 0.5H, J=7 Hz), 1.65 (d, 1.5H, J=7 Hz), 1.64 (d, 1.5H, J=7 Hz).

MS(Cl, Isobutane): 339, 341 (5, MH$^+$, M+2H$^+$), 318 (42), 227 (25), 260 (82), 235 (95), 199 (35), 182 (55), 155 (100).

IR(KBr) cm$^{-1}$: 3220 br, 1600, 1390, 1165, 825, 790

Anal. Calcd. for C$_{13}$H$_{11}$BrN$_2$O$_2$S: C, 46.03; H, 3.27; N, 8.26%. Found: C, 46.34; H, 3.42; N, 8.23%.

EXAMPLE 2

4-[1-(3-Methyl-2-naphthalenyl)ethyl]-3H-1,2,3,5-oxathiadiazole 2-Oxide (Step 1) Preparation of
2-Hydroxymethyl-3-methylnaphthalene To a stirred solution of 3-methylnaphthalene-2-carboxaldehyde (3.40 g, 20 mmol) in dry THF (200 mL) cooled to 0° C. was added lithium aluminum hydride (LAH, 380 mg, 10 mmol), in portions over 10 minutes. The resulting solution was stirred at 0° C. for 1.5 hours. Excess LAH was quenched by the addition of H$_2$O (50 mL) and the THF was removed in vacuo. The residue was diluted with 1N HCl (150 mL) and extracted with Et$_2$O (3×200 mL). The organics were dried (MgSO$_4$) and concentrated in vacuo to give the crude product as a tan solid. This material was purified by preparative HPLC (SiO$_2$: 1:1 CH$_2$Cl$_2$/hexane) to afford the title compound as a white solid (2.47 g, 72%).

NMR (300 MHz, CDCl$_3$): δ 7.80 (m, 3H), 7.60 (s, 1H), 7.42 (m, 2H), 4.85 (s, 2H), 2.48 (s, 3H), 1.65 (br s, 1H).

(Step 2) Preparation of
2-Bromomethyl-3-methylnaphthalene

To a stirred solution of 2-hydroxymethyl-3-methylnaphthalene (2.47 g, 14.4 mmol) in dry Et$_2$O (50 mL) cooled to 0° C. was added phosphorus tribromide (4.88 g, 18 mmol) dropwise over 20 minutes. The resulting heterogeneous mixture was stirred at 0° C. for 1.25 hours and then quenched with H$_2$O (50 mL). The reaction mixture was diluted further with H$_2$O (50 mL) and extracted with Et$_1$O (2×150 mL). The combined organic layers were washed with H$_2$O (1×100 mL), dried (MgSO$_4$) and concentrated in vacuo. The residue was purified by filtration through silica gel using CH$_2$Cl$_2$ as eluent to give the product as an off-white solid (2.94 g, 87%).

NMR (300 MHz, CDCl$_3$): δ7.82 (s, 1H), 7.77 (m, 2H), 7.65 (s, 1H), 7.44 (m, 2H), 4.70 (s, 2H), 2.60 (s, 3H).

(Step 3) Preparation of
(3-Methyl-2-naphthalenyl)acetonitrile

A suspension of 2-bromomethyl3-methylnaphthalene (2.87 g, 12.2 mmol) and NaCN (652 mg, 13.3 mmol) in CH$_3$CH/H$_2$O (9:1, 125 mL) was heated to reflux for 1 hour. Upon warming, the suspension became homogeneous. After cooling to room temperature, the volatiles were removed from the reaction mixture in vacuo and the residue was partitioned between $_2$O (150 mL) and CH$_2$Cl$_2$ (150 mL). The aqueous phase was extracted with CH$_2$Cl$_2$ (1×150 mL). The combined organic layers were dried (Na$_2$SO$_4$) and concentrated in vacuo to give the title compound as a white solid (2.18 g, 99%). This material was of sufficient purity to be used as such in the next step.

NMR (200 MHz, CDCl$_3$): δ7.88 (s, 1H), 7.81 (m, 2H), 7.68 (s, 1H), 7.49 (m, 2H), 3.84 (s, 2H), 2.50 (s, 3H).

(Step 4) Preparation of
2-(3-Methyl-2-naphthalenyl)propionitrile

To a stirred solution of (3-methyl-2-naphthalenyl)acetonitrile (2.17 g, 12 mmol) in dry THF (125 mL) cooled to −78° C. was added n-BuLi (8.44 mL, 13.5 mmol; 1.6M solution in hexanes)dropwise over 10 minutes. The resulting orange solution was stirred for 20 minutes at −78° C. and MeI (1.92 g, 13.5 mmol) was added in one portion. The reaction mixture was stirred at −78° C. for 1.25 hours and quenched with saturated NH$_4$Cl (20 mL). After warming to room temperature, the volatiles were removed in vacuo and the residue was diluted with H$_2$O (150 mL). The aqueous phase was extracted with Et$_2$O (2×150 mL). The combined organic layers were washed with saturated NaCl (1×150 mL) and dried (MgSO$_4$). Removal of the solvent in vacuo afforded the product as a light yellow solid (2.34 g, 100%). This material was of sufficient purity to be used as such.

NMR (300 MHz, CDCl$_3$): δ7.94 (s, 1H), 7.82 (m, 1H), 7.75 (m, 1H), 7.66 (s, 1H), 7.46 (m, 2H), 4.17 (q, 1H, J=7 Hz), 2.52 (s, 3H), 1.71 (d, 3H, J=7 Hz).

(Step 5) Preparation of
N'-Hydroxy-2-(3-methyl-2-naphthalenyl)propanimidamide

According to General Procedure A, 2-(3-methyl-2-naphthalenyl)propionitrile (2.34 g, 12 mmol) was refluxed for 5 days to obtain the desired product (2.74 g, 100%) as a yellow oil used as such in the next step.

NMR (300 MHz, CDCl$_3$): δ 7.76 (m, 3H), 7.64 (s, 1H), 7.44 (m, 2H), 6.18 (br s, 1H), 4.50 (br s, 2H), 4.02 (q, 1H, J=7 Hz), 2.52 (s, 3H), 1.64 (d, 3H, J=7 Hz).

(Step 6) Preparation of
4-[1-(3-Methyl-2-naphthalenyl)ethyl]-3H-1,2,3,5-oxathiadiazole 2-Oxide According to General Procedure B, N'-hydroxy-2-(3-methyl-2-naphthalenyl)propanimidamide (2.28 g, 10 mmol) was converted to the desired product as a white solid (1.48 g, 54%). Trituration with CH$_2$Cl$_2$ gave an analytically pure product, m.p. 167° C. (dec.).

NMR (400 MHz, DMSO-d$_6$):1:1 mixture of diastereomers δ 11.31 (br s, 1H), 7.80 (m, 1H), 7.73 and 7.66 (2 s, 2H total area), 7.44 (m, 2H), 4.49 (q, 0.5H, J=7 Hz), 4.42 (q, 0.5H, J=7 Hz), 2.49 (s, 3H), 1.61 (d, 3H, J=7 Hz).

MS (EI, 70 ev): 274 (41, M+), 195 (100), 180 (56), 169 (96), 154 (57), 141 (30).

IR (KBr)cm$^{-1}$: 3120, 1605, 1410, 1202, 750.

Anal. Calcd. for $C_{14}H_{14}N_2O_2S$: C, 61.29; H, 5.14; N, 10.21%. Found: C, 61.35; H, 5.20; N, 9.98%.

EXAMPLE 3

4-[1-Methyl-2-(2-naphthalenyl)ethyl]-3H-1,2,3,5-oxathiadiazole 2-Oxide (Step 1) Preparation of
2-Methyl-3-(2-naphthalenyl)propionitrile To a stirred solution of naphthalenylpropionitrile (4.52 g, 25 mmol) in dry THF (250 mL) at −78° C. was added n-BuLi (18.75 mL, 30 mmol; 1.6M solution in hexanes) dropwise over 20 minutes. The resulting solution was stirred for 20 minutes at −78° C. and the MeI (4.26 g, 30 mmol) was added in one portion. The reaction mixture was stirred for 20 minutes at −78° C. and quenched by the addition of saturated NH$_4$Cl (35 mL). After warming to room temperature, the volatiles were removed in vacuo, the residue diluted with H$_2$O (20 mL) and extracted with Et$_2$O (2×250 mL). The organics were washed with H$_2$O (1×250 mL), dried (MgSO$_4$) and concentrated in vacuo. The crude product was purified by preparative HPLC (SiO$_2$: gradient hexane/CH$_2$Cl$_2$) to give the title compound as a white solid (3.21 g, 66%).

NMR (300 MHz, CDCl$_3$): δ7.82 (m, 3H), 7.70 (s, 1H), 7.48 (m, 2H), 7.35 (d, 1H), 3.11 (m, 1H), 2.97 (m, 2H), 1.36 (d, 3H).

(Step 2) Preparation of
N'-Hydroxy-2-methyl-3-(2-naphthalenyl)propanimidamide

According to General Procedure A, 2-methyl-3-(2-naphthalenyl)propionitrile (3.20 g, 16 mmol) was refluxed for 5 days to obtain the desired product in 70% yield (by NMR) as a yellow oil. The crude product was used as such in the next step.

(Step 3) Preparation of
4-[1-Methyl-2-(2-naphthalenyl)ethyl]-3H-1,2,3,5-oxathiadiazole 2-Oxide According to General Procedure B, the crude N'-hydroxy-2-methyl-3-(2-naphthalenyl)propanimidamide (3.74 g, 16 mmol) was converted to the desired product as a light yellow oil (2.58 g, 57%, yield calculated from the nitrile). The product was purified by flash chromatography on SiO$_2$ with CH$_2$Cl$_2$ eluant to afford analytically pure material.

NMR (400 MHz, DMSO-d$_6$): δ 7.82 (m, 3H), 7.69 (s, 1H), 7.46 (m, 2H), 7.38 (dd, 1H, J=1,8), 3.20 (m, 2H), 2.95 (m, 1H), 1.22 (d, 3H, J=7 Hz).

MS (EI, 70 ev): 274 (5, M+), 210 (6), 195 (7), 168 (63), 156 (28), 141 (100), 115 (32).

Anal. Calcd. for $C_{14}H_{14}N_2O_2S$: C, 61.29; H, 5.14; N, 10.21%. Found: C, 60.94; H, 5.04; N, 10.08%.

EXAMPLE 4

4-[1-(2-Naphthalenyl)ethyl]-3H-1,2,3,5-oxathiadiazole 2-Oxide (Step 1) Preparation of 2(2-Naphthalenyl)propionitrile and 2-Methyl-2-(2-naphthalenyl)propionitrile According to the procedure of W. G. Kenyon et al *J. Org. Chem.* 30, 2937 (1965), to a refluxing suspension of NaH (3.00 g, 75 mmol, 60% dispersion) in DME (150 mL) was added a solution of 2-naphthylacetonitrile (12.5 g, 75 mmol) and methyl iodide (10.65 g, 75 mmol, 4.67 mL) in DME (75 mL) dropwise over 1 hour. The resulting dark solution was refluxed for 3 hours and cooled to room temperature. The DME was removed in vacuo. The residue was dissolved in Et$_2$O (200 mL) and partitioned with H$_2$O (150 mL). The layers were separated, the aqueous phase washed with Et$_2$O (2×200 mL) and the combined organic layers were dried (MgSO$_4$) and concentrated in vacuo to give a dark oil. This residue was purified by preparative HPLC (SiO$_2$: gradient elution with hexane/EtOAc) to give 2-methyl-2-(2-naphthalenyl)propionitrile (2.28 g, 20%) as a light yellow oil. Further elution provided 2-(2-naphthalenyl)propionitrile (5.68 g, 42%) as a white solid.

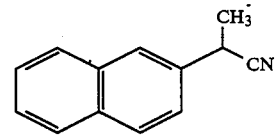

NMR (200 MHz, CDCl$_3$): δ 7.87 (m, 4H), 7.49 (m, 3H), 4.03 (q, 1H, J=7 Hz), 1.75 (d, 3H, J=7 Hz).

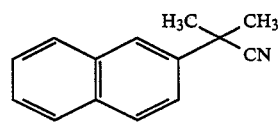

NMR (200 MHz, CDCl$_3$): δ 7.95 (s, 1H), 7.85 (m, 3H), 7.55 (m, 3H), 1.80 (s, 6H).

(Step 2) Preparation of
N'-Hydroxy-2-(2-naphthalenyl)propanimidamide

According to General Procedure A, 2-(2-naphthalenyl)propionitrile (5.07 g, 28 mmol) was refluxed for 3 days to obtain the desired product (5.87 g, 98%) as a light yellow oil and used as such in the next step without purification.

NMR (200 MHz, CDCl$_3$): δ 9.28 (br s, 1H), 7.75 (m, 4H), 7.42 (m, 3H), 4.45 (br s, 2H), 3.75 (q, 1H, J=7 Hz), 1.52 (d, 3H, J=7 Hz).

(Step 3) Preparation of
4-[1-(2-Naphthalenyl)ethyl]-3H-1,2,3,5-oxathiadiazole 2-Oxide According to General Procedure B, N'-hydroxy-2-(2-naphthalenyl)propanimidamide (4.18 g, 20 mmol) was converted to the desired product by reaction for 30 minutes at 0° C. The product was purified by flash chromatography of SiO$_2$ eluted with CH$_2$Cl$_2$, followed by EtOAc/CH$_2$Cl$_2$ (0.5: 99.5), EtOAc/CH$_2$Cl$_2$ (1.99), and EtOAc/CH$_2$Cl$_2$ (2:99) to afford the title compound as a yellow oil (2.45 g, 48%).

NMR (400 MHz, CDCl$_3$): 1:1 mixture of diastereomers δ7.84 (m, 3H), 7.73 (d, 1H, J=8 Hz), 7.51 (m, 2H), 7.37 (dd, 0.5H, J=8, 1.5 Hz), 7.33 (dd, 0.5H, J=8, 1.5 Hz), 6.85 (br s, 1H), 4.29 (q, 0.5H, J=6 Hz), 4.15 (q, 0.5H, J=6 Hz), 1.78 (d, 1.5H, J=6 Hz), 1.77 (d, 1.5H, J=6 Hz).

MS (EI, 70 ev): 260 (50, M+), 196 (30), 181 (62), 155 (100), 127 (15).

IR (KBr) cm$^{-1}$: 3380 br, 3240 br, 1380, 1170, 820.

Anal. Calcd. for $C_{13}H_{12}N_2O_2S \cdot 0.025CCl_4$: C, 59.22; H, 4.58; N, 10.61%. Found: C, 59.30; H, 4.74; N, 10.24%.

EXAMPLE 5

4-[(2-Naphthalenylthio)methyl]-3H-1,2,3,5-oxathiadiazole 2-Oxide (Step 1) Preparation of 2-Naphthalenylthioacetonitrile To a stirred suspension of 2-naphthalenethiol (7.20 g, 45 mmol) and $K_2CO_3$ (6.90 g, 50 mmol) in acetone (350 mL) was added chloroacetonitrile (3.78 g, 50 mmol) in acetone (50 mL) dropwise over 30 minutes. The resulting yellow mixture was stirred at room temperature for 18 hours. The volatiles were removed in vacuo and the residue was partitioned between EtOAc (300 mL) and $H_2O$ (300 mL). The aqueous phase was washed with EtOAc (1×250 mL) and the combined extracts were dried ($Na_2SO_4$) and concentrated in vacuo. The crude material was purified by preparative HPLC ($SiO_2$: gradient EtOAc/hexane) to give the title compound as a light brown solid (5.86 g, 65%).

NMR (200 MHz, $CDCl_3$): δ 8.05 (s, 1H), 7.81 (m, 3H), 7.54 (m, 3H), 3.61 (s, 2H).

(Step 2) Preparation of N′-Hydroxy-2-(2-naphthalenylthio)ethanimidamide

According to General Procedure A, (4.8 g, 25 mmol) was stirred at room temperature for 6 days. The reaction mixture was poured into water (500 mL) and the precipitated product collected by suction and dried in vacuo at 50° C. overnight to give the desired compound as a white solid (5.68 g, 98%). This material was used as such without further purification.

NMR (200 MHz, DMSO-$d_6$);δ9.16 (s, 1H), 7.81 (m, 4H), 7.46 (m, 3H), 5.55 (br s, 2H), 3.66 (s, 2H).

(Step 3) Preparation of 4-[(2-Naphthalenylthio)methyl]-3H-1,2,3,5-oxathiadiazole 2-Oxide According to General Procedure B, N′-hydroxy-2-(2-naphthalenylthio)ethanimidamide (4.64 g, 20 mmol) was converted to the desired product. This material was purified by flash chromatography on $SiO_2$ eluted with $CH_2Cl_2$ followed by $Et_2O$ trituration to give the title compound as a white solid (2.02 g, 36%) m.p. 102°–103° C. (dec.).

NMR (400 MHz, DMSO-$d_6$): δ11.6 (br s, 1H), 7.95 (s, 1H), 7.88 (m, 2H), 7.82 (m, 2H), 7.51 (m, 3H), 4.27 (d, 2H, J=1.5 Hz)

MS (EI, 70 ev): 278 (14, M+), 199 (13), 173 (33), 168 (65), 159 (58), 128 (23), 115 (100).

IR (KBr) $cm^{-1}$: 3140 br, 1410, 1390, 1200, 810.

Anal. Calcd. for $C_{12}H_{10}N_2O_2S_2$: C, 51.78; H, 3.62; N, 10.06%. Found: C, 51.55; H, 3.66; N, 9.67%.

EXAMPLE 6

4-[2-(2-Naphthalenyl)propyl]-3H-1,2,3,5-oxathiadiazole 2-Oxide (Step 1) Preparation of 3-Methyl-3-(2-naphthalenyl)acrylonitrile To a suspension of NaH (2.40 g, 60 mmol, 60% dispersion) in dry THF (300 mL) at 0° C. was added a solution of diethyl cyano methyl phosphonate (7.79 g, 44 mmol) in THF (50 mL) dropwise over 35 minutes. The resulting solution was stirred at 0° C. for 5 minutes and a solution of naphthalenylmethylketone (6.80 g, 40 mmol) in THF (50 mL) was then added over 35 minutes. The resulting brown solution was stirred at 0° C. for 1 hour and then quenched at 0° C. by the dropwise addition of $H_2O$ (100 mL). The volatiles were removed in vacuo and the residue was diluted with $H_2O$ (300 mL). The aqueous mixture was extracted with $Et_2O$ (2×400 mL), the combined organic layers washed with $H_2O$ (1×300 mL), dried ($MgSO_4$) and concentrated in vacuo to give a light yellow oil (8.75 g). Crude NMR indicated a 29:1 ratio of desired product to naphthalenylmethylketone. This material was used as such in the subsequent step without further purification.

NMR (200 MHz, $CDCl_3$): δ7.85 (m, 4H), 7.50 (m, 3H), 5.75 (s, 1H), 2.52 (s, 3H).

(Step 2) Preparation of 3-(2-Naphthalenyl)butyronitrile

The crude 3-methyl-3(2-naphthalenyl)acrylonitrile (8.75 g) was hydrogenated over 5% Pd/C (770 mg) in EtOH (400 mL) at 50 PSIG until the reaction was complete by TLC (about 3 days). The reaction mixture was filtered through Solka-floc® and concentrated in vacuo to give a yellow oil. The crude material was purified by flash chromatography ($SiO_2$) with elution by hexane/$CH_2Cl_2$ (2:1), followed by hexane/$CH_2Cl_2$ (3:2), to give the product as a colorless oil 6.60 g, 85% yield calculated from the naphthalenylmethylketone).

NMR (300 MHz, $CDCl_3$): δ 7.85 (m, 3H), 7.70 (s, 1H), 7.50 (m, 2H), 7.38 (d, 1H), 3.35 (m, 1H), 2.70 (m, 2H), 1.59 (d, 3H).

(Step 3) Preparation of N′-Hydroxy-3-(2-naphthalenyl)butanimidamide

According to General Procedure A, 3-(2-naphthalenyl)butyronitrile (6.63 g, 34 mmol) was refluxed for 4 days to obtain a yellow oil containing a 3:1 ratio of product to starting material (determined by NMR). This crude material was used as such in the next step.

(Step 4) Preparation of 4-[2-(2-Naphthalenyl)propyl]-3H-1,2,3,5-oxathiadiazole 2-Oxide According to General Procedure B, N′-hydroxy-3-(2-naphthalenyl)butanimidamide (3.17 g crude, 2.38 g based on 75% purity, 11 mmol) was converted to the desired product. The product was purified by flash chromatography on $SiO_2$ eluted with $CH_2Cl_2$ to give the title compound as a whit solid (2.11 g, 71%), m.p. 99°–101° C.

NMR (400 MHz, $CDCl_3$): δ 7.82 (m, 3H), 7.66 (s, 1H), 7.48 (m, 2H), 7.36 (d, 1H, J=8 Hz), 7.00 (2 br s, 1H), 3.29 (m, 1H), 2.96 (m, 2H), 1.44 (2d, 3H, J=5 Hz).

MS [(+)-FAB, GLYCEROL/DMSO]: 275 (40, M+H+),

IR (KBr)$cm^{-1}$: 3100 (br), 1600, 1410, 1200.

Anal. Calcd. for $C_{14}H_{14}N_2O_2S$: C, 61.29; H, 5.14; N, 10.21%. Found: C, 61.04; H, 5.26; N, 10.15%.

EXAMPLE 7

4[1-Methyl-1-(2-naphthalenyl)ethyl]-3H-1,2,3,5-oxathiadiazole 2-Oxide (Step 1) Preparation of N′-Hydroxy-2-methyl-2-(2-naphthalenyl)propanimidamide According to General Procedure A, 2-methyl-2-(2-naphthalenyl)propionitrile 2.88 g, 15 mmol) was refluxed for 4 days to obtain crude product which was purified by trituration with $Et_2O$ to obtain the desired product as a white solid (1.68 g, 50%).

NMR (200 MHz, DMSO-d6): δ9.20 (s, 1H), 7.82 (m, 4H), 7.45 (m, 3H), 6.90 (br s, 1H), 5.15 (br s, 1H), 1.52 (s, 6H).

(Step 2) Preparation of 4-[1-Methyl-1-(2-naphthalenyl)ethyl]-3H-1,2,3,5-oxa-thiadiazole 2-Oxide According to General Procedure B, N'-hydroxy-2-methyl-2-(2-naphthalenyl)propanimidamide (1.81 g, 8 mmol) was converted to the desired product. This material was purified by flash chromatography of SiO2 with CH2Cl2 eluent to give the title compound as a white solid (970 mg, 45%), m.p. 146°-147° C.

NMR (400 MHz, DMSO-d6): δ11.82 (s, 1H), 7.90 (m, 4H), 7.52 (m, 2H), 7.43 (dd, 1H, J=8, 1.5 Hz), 1.74 (s, 3H), 1.73 (s, 3H).

MS (EI, 70 ev): 274 (15, M+), 195 (90), 169 (88), 153 (100), 141 (95), 128 (70).

IR (KBr) cm−1: 3310, 1470, 1370, 1190.

Anal. Calcd. for $C_{14}H_{14}N_2O_2S$: C, 61.29; H, 5.14; N, 10.21%. Found: C, 61.20; H, 5.25; N, 10.31%.

EXAMPLE 8

4-[1-(2-Naphthalenyl)-2-phenylethyl]-3H-1,2,3,5-oxa-thiadiazole 2-Oxide (Step 1) Preparation of 2-(2-Naphthalenyl)-3-phenylpropionitrile To a refluxing solution of NaH (3.00 g, 75 mmol, 60% dispersion) in DME (150 mL) was added a solution of 2-naphthaleneacetonitrile (12.5 g, 75 mmol) and benzyl bromide (12.8 g, 75 mmol) in DME (75 mL) dropwise over 50 minutes. The resulting solution was kept at reflux for 3 hours and then cooled to room temperature. The volatiles were removed in vacuo and the residue was partitioned between Et2O (100 mL) and H2O (100 mL). The aqueous phase was washed with Et2O (1×150 mL), the organics were dried (MgSO4) and concentrated in vacuo. This residue was purified by preparative HPLC (SiO2: gradient hexane/EtOAc) to give the title compound as a white solid (7.71 g, 40%).

NMR (200 MHz, CDCl3): δ 7.82 (m, 3H), 7.75 (s, 1H), 7.55 (m, 2H), 7.21 (m, 6H), 4.18 (t, 1H, J=7 Hz), 3.25 (m, 2H).

(Step 2) Preparation of N'-Hydroxy-2-(2-naphthalenyl)-3-phenylpropanimidamide

According to General Procedure A, 2-(2-naphthalenyl)-3-phenylpropionitrile (1.01 g, 4 mmol) was converted to the desired product as a white foam 1.13 g, 100%) and used in the next step as such without any purification.

(Step 3) Preparation of 4-[1-(2-Naphthalenyl)-2-phenylethyl]-3H-1,2,3,5-oxa-thiadiazole 2-Oxide According to the General Procedure B, N'-hydroxy-2-(2-naphthalenyl)-3-phenylpropanimidamide (1.13 g, 4 mmol) was converted to the desired product. This material was purified by flash chromatography of SiO2 eluted with CH2Cl2 to give the title compound as a white solid (900 mg, 69%).

NMR (200 MHz, CDCl3): 1:1 mixture of diastereomers δ 7.80 (m, 3H), 7.55 (m, 3H), 7.25 (m, 4H), 7.10 (m, 2H), 6.85 (br s, 1H), 4.32 (dd, 0.5H, J=6,8 Hz), 4.18 (dd, 0.5H, J=6,8 Hz), 3.71 (dd, 0.5H, J=2,6 Hz), 3.64 (dd, 0.5H, J=2,6 Hz), 3.32 (m, 1H) MS (EI, 70 ev): 336 (4.1, M+), 257 (13), 181 (30), 166 (16), 91 (100), 64 (21)

IR (KBr) cm−1: 3210 (br), 1600, 1385, 1260, 810.

Anal. Calcd. for $C_{19}H_{16}N_2O_2S$: C, 67.83; H, 4.79; N, 8.33%. Found: C, 67.93; H, 4.86; N, 8.25%.

EXAMPLE 9

4-[2-Methoxy-2-(2-naphthalenyl)ethyl]-3H-1,2,3,5-oxa-thiadiazole 2-Oxide (Step 1) Preparation of 3-Hydroxy-3-(2-naphthalenyl)propionitrile To a stirred solution of acetonitrile (2.46 g, 60 mmol, 3.13 mL) in THF (300 mL) at −78° C. was added N-BuLi (37.5 mL, 60 mmol, 1.6M) dropwise over 30 minutes. The resulting solution was stirred at −78° C. for 15 minutes and then 2-naphthaldehyde (6.24 g, 40 mmol) in THF (50 mL) was added dropwise over 45 minutes. The resulting mixture was stirred for an additional 20 minutes at −78° C. and quenched at −78° C. by the addition of saturated NH4Cl (60 mL). The mixture was warmed to room temperature and the THF removed in vacuo to give a white solid. The residue was partitioned between CH2Cl2 (250 mL) and H2O (200 mL, the layers were separated and the aqueous phase extracted with CH2Cl2 (1×250 mL). The combined organic layers were washed with H2O (1×250 ML), dried (Na2SO4) and concentrated in vacuo to give the title compound as a tan solid (7.88 g, 100%) which was homogeneous by TLC and NMR. This material was used as such without purification.

NMR (200 MHz, CDCl3): δ 7.80 (m, 4H), 7.45 (m, 3H), 5.08 (m, 1H), 3.05 (br d, 1H, J=2 Hz), 2.75 (d, 2H, J=7 Hz).

(Step 2) Preparation of 3-Methoxy-3-(2-naphthalenyl)propionitrile

To a suspension of NaH (1.50 g, 37.5 mmol, 60% dispersion) in dry THF (200 mL) cooled to 0° C. was added 3-hydroxy-3-(2-naphthalenyl)propionitrile (4.92 g, 25 mmol) in THF (50 mL) dropwise over 20 minutes. The resulting solution was stirred at 0° C. for 5 minutes and dimethylsulfate (4.72 g, 37.5 mmol) was added in one portion. The reaction mixture was stirred at 0° C. for 20 minutes and room temperature for 1.5 hours. The reaction was then diluted with H2O (50 mL) and the volatiles were removed in vacuo. The residue was partitioned between CH2Cl2 (250 mL) and H2O (200 mL). The aqueous phase was extracted with CH2Cl2 (1×250 mL), the combined organic layers dried (Na2SO4) and concentrated in vacuo to give a thick yellow oil. This was purified by preparative HPLC (SiO2: gradient EtOAc/hexane) to give the product as a light yellow oil (4.58 g, 87%).

NMR (200 MHz, CDCl3): δ 7.88 (m, 4H), 7.51 (m, 3H), 4.62 (t, 1H, J=7 Hz), 3.32 (s, 3H), 2.80 (m, 2H).

(Step 3) Preparation of N'-Hydroxy-3-methoxy-3(2-naphthalenyl)propanimidamide

According to General Procedure A, 3-methoxy-3-(2-naphthalenyl)propionitrile(4.15 g, 20 mmol) was refluxed for 5 days and the crude product purified by flash chromatography on SiO2 eluted with CH2Cl2, followed by MeOH/CH2Cl2 (1:99), and MeOH/CH2Cl2 (2:98), to obtain the pure product as a light yellow oil (3.60 g, 75%).

NMR (300 MHz, CDCl₃): δ 9.13 (br s, 1H), 7.85 (m, 3H), 7.77 (s, 1H), 7.47 (m, 3H), 5.13 (br s, 2H), 4.60 (dd, 1H), 3.28 (s, 3H), 2.71 (dd, 1H), 2.50 (dd, 1H).

(Step 4) Preparation of
4-[2-Methoxy-2-(2-naphthalenyl))ethyl]-3H-1,2,3,5-oxathiadiazole 2-Oxide According to General Procedure B, N'-hydroxy-3-methoxy-3-(2-naphthalenyl)propanimidamide (260 mg, 1 mmol) was converted to the desired analytically pure product (255 mg, 83%) m.p. 137°–138° C. (dec.) without any purification.

NMR (400 MHz, DMSO-d₆): δ 11.38 (br s, 1H), 7.92 (m, 3H), 7.85 (s, 1H), 7.52 (m, 3H), 4.73 (dd, 1H, J=5,8 Hz), 3.16 (2s, 3H), 3.10 (m, 1H), 2.95 (m, 1H).

MS (EI, 70 ev): 290 (0.5, M+), 240 (1), 211 (10), 194 (20), 171 (100), 155 (30), 127 (35).

IR (KBr) cm⁻¹: 3440 (br), 3120 (br), 1605, 1415, 1195, 1005, 995.

Anal. Calcd. for $C_{14}H_{14}N_2O_3S$: C, 57.92; H, 4.86; N, 9.65%. Found: C, 57.80; H, 4.92; N, 9.36%.

EXAMPLE 10

4-[(2-Naphthalenylsulfonyl)methyl]-3H-1,2,3,5-oxathiadiazole 2-Oxide (Step 1) Preparation of
N'-Hydroxy-(2-naphthalenyl)sulfonylethanimidamide According to General Procedure A, hydroxylamine hydrochloride (2.26 g, 32.5 mmol), was added in one portion to a solution of NaOMe, freshly prepared from sodium (0.75 g, 32.5 mmol) in methanol. The resulting mixture was stirred 1 hour at room temperature, during which time a precipitate was formed. (2-Naphthalenylsulfonyl)acetonitrile (3.0 g, 13.0 mmol), was added in one portion and the resulting mixture heated to reflux a total of 24 hours. The mixture was cooled to room temperature and then to 0° C. to give a precipitate. The precipitate was collected by filtration, washed with water, and dried in vacuo to give a white crystalline solid (2.75 g, 80%) which was of sufficient purity for use in the subsequent reaction.

NMR (DMSO-d₆): δ 9.33 (s, 1H), 8.50 (s, 1H), 8.17 (d, J=8.7, 1H), 8.13 (d, J=8.0, 1H), 8.05 (d, J=8.0, 1H), 7.85 (d, J=8.7, 1H), 7.67 (m, 2H), 5.50 (br s, 2H), 4.09 (s, 2H).

(Step 2) Preparation of
4-[(2-Naphthalenylsulfonyl)methyl]-3H-1,2,3,5-oxathiadiazole 2-Oxide A suspension of N'-hydroxy-(2-naphthalenyl)sulfonylethanimidamide (2.7 g, 10.2 mmol), in 300 mL toluene was heated to 80° C. until all of the solid had dissolved. Thionyl chloride (1.46 g, 12.3 mmol) was added dropwise to the above solution under a stream of nitrogen, and a white precipitate was formed. The mixture was heated to reflux for 60 minutes, during which time the precipitate dissolved to give an orange solution. The hot solution was filtered to remove trace solids and the filtrate was allowed to stand at room temperature. The desired product (2.05 g, 65%) crystallized as a tan solid which was collected by filtration and dried in vacuo, m.p. 170°–171° C. (dec.).

NMR (DMSO-d₆: δ 11.55 (br s, 1H), 8.53 (s, 1H), 8.17 (d, J=8.7, 1H) 8.16 (d, J=8.0, 1H), 8.09 (d, J=8.0, 1H), 7.85 (d, J=8.7, 1H), 7.77 (t, J=8.0, 1H), 7.71 (t, J=8.0, 1H), 4.99 (d, J=14.4, 1H), 4.93 (d, J=14.4, 1H).

IR (KBr) cm⁻¹: 3120, 3000, 2920, 1410, 1325, 1170, 1120.

MS (CI): 311 (M+H, 100), 232 (40).

Anal. Calcd. for $C_{12}H_{10}N_2O_4S_2$: C, 46.44; H, 3.25; N, 9.03%. Found: C, 46.59; H, 3.52; N, 9.05%.

The blood glucose lowering activity of the compounds of this invention was demonstrable in experiments using diabetic (db/db) mice. The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman Diabetes 31 (Suppl. 1), 1 (1982)]. In spite of these commonalities, the acute administration of sulfonylureas (even at extremely high dosages) will not reduce the hyperglycemia of the db/db mouse. [See Tutwiler et al, Diabetes 27, 856 (1978)]. The ability of a few other hypoglycemic agents to be effective in this species suggest that the other agents have mechanisms of action which are different from that of the sulfonylureas [ibid; Lee et al, Diabetes 31:12 (1982); Chang et al, Diabetes 32, 830 (1983); Hosokawa et al, Diabetes 34, 267 (1985)]. Such compounds, therefore, are more likely to be efficacious in the population of Type II diabetic patients that do not respond to sulfonylurea therapy. The experimental results are exemplified hereinbelow after the listing of the following general procedure pertaining to these experiments.

POSTPRANDIAL ASSAY PROCEDURE

On the morning of Day 1, 35 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbot VP Analyser. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels:

| Group A: | Vehicle control | N = 6 |
|---|---|---|
| Group B: | Positive control (ciglitazone) | N = 4 |
| Group C: | 1st Test drug | N = 4 |
| Group D: | 2nd Test drug | N = 4 |
| Group E: | 3rd Test drug | N = 4 |
| Group F: | 4th Test drug | N = 4 |
| Group H: | 5th Test drug | N = 4 |

On the afternoon of Days 1, 2 and 3 the vehicle, control or test drugs were administered (p.o.) to the ad libitum fed mice. The positive control, ciglitazone [(±)-5-[4-[(1-methylcyclohexy]methoxyl]benzyl]-thiazolidine-2,4-dione] see Fujita et al., Diabetes 32 804 (1983), was given by gavage at a dose of 100 mg/kg/day. The test compounds were given by gavage at a dose of 100 mg/kg/day unless otherwise noted in Table 1.

On the morning of Day 4, the mice were weighed and food removed, but water was availably ad libitum.

Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyser.

For each mouse, the percent change of its plasma glucose on Day 4 (mean of the 2 and 4 hour samples) from its respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle control group and the individual drug-treated groups.

The tabulated results in Table 1 show that the oxathiadiazoles of this invention show the property that they lower blood glucose levels in the postprandial diabetic (db/db) mice. The actual difference between the mean percent change of the vehicle and the drug-treated group is reported in Table 1.

Examination of the results tabulated in Table 1 below shows that the oxathiadiazoles of this invention are well suited as antihyperglycemic agents for they lower blood glucose levels in diabetic mice. For example, 4-[1-(5-bromo-2-naphthalenyl)ethyl]-3H-1,2,3,5-oxathiadiazole 2-oxide, the compound of Example 1, at a dose of 5 mg/kg/day give comparable results to ciglitazone at 100 mg/kg/day.

TABLE 1

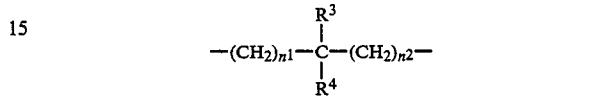

| $R^1$ | $R^2$ | Z | Dose mg/kg/day | % Change from Vehicle in Postprandial Plasma Glucose | m.p.°C. |
|---|---|---|---|---|---|
| 5-Br | —H | 2-CH(CH$_3$)— | 1 | −27 | glassy solid |
|  |  |  | 5 | −41 |  |
| 3-CH$_3$ | —H | 2-CH(CH$_3$)— | 1 | −19 | 167 (dec.) |
| —H | —H | 2-CH$_2$CH(CH$_3$)— | 5 | −22 | oil |
| —H | —H | 2-CH(CH$_3$)— | 20 | −49 | oil |
| —H | —H | 2-SCH$_2$— | 20 | −40 | 102-103 (dec.) |
| —H | —H | 2-CH(CH$_3$)CH$_2$— | 20 | −27 | 99-101 |
| —H | —H | 2-C(CH$_3$)$_2$— | 20 | −14 | 146-147 |
| —H | —H | 2-CH(CH$_2$Ph)— | 20 | −8 | 61-62 |
| —H | —H | 2-CH(OCH$_3$)CH$_2$— | 20 | −6 | 137-138 (dec.) |
| —H | —H | 2-SO$_2$CH$_2$— | 20 | −3 | 170-171 |
| —H | —H | 2-O—CH$_2$ | 20 | 4 | 101-103 |
| —H | —H | 2-CH=CH— | 5 | 4 | 146-147 (dec.) |
| Ciglitazone |  |  | 100 | −33 |  |

We claim:

1. A compound of structural formula (I)

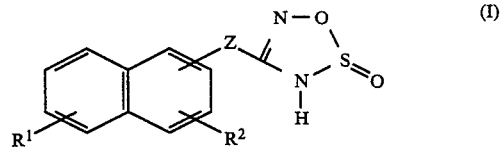

wherein $R^1$ and $R^2$ are independently hydrogen, lower alkyl containing 1 to 6 carbon atoms, alkoxy containing 1 to 6 carbon atoms, ethynyl, methylthio, nitro or halogen; Z is $$-(CH_2)_{n1}-\underset{\underset{R^4}{|}}{\overset{\overset{R^3}{|}}{C}}-(CH_2)_{n2}-$$

wherein $R^3$ is hydrogen, lower alkyl containing 1 to 3 carbon atoms, alkoxy containing 1 to 2 carbon atoms, or benzyl; $R^4$ is lower alkyl containing 1 to 3 carbon atoms, alkoxy containing 1 to 2 carbon atoms, or benzyl; $n^1$ is 0, 1, or 2; $n^2$ is 0, 1, or 2; or Z is —S—CH$_2$—, —SO$_2$—CH$_2$-, or —OCH$_2$—; or Z is —C(R$^5$)=C(R$^6$)—, wherein $R^5$ and $R^6$ are independently hydrogen or lower alkyl containing 1 to 3 carbon atoms, or the pharmaceutically acceptable salts thereof.

2. A compound according to claim 1 of structural formula (II)

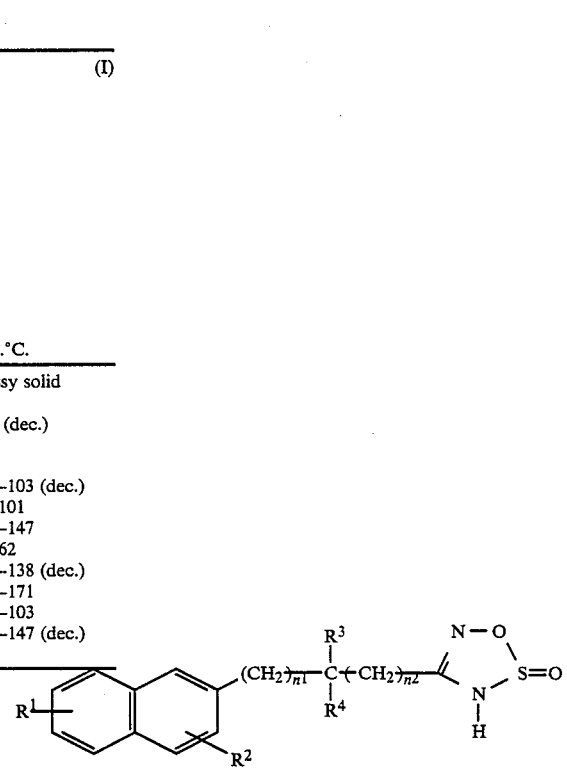

wherein $R^1$ and $R^2$ are independently hydrogen, lower alkyl containing 1 to 6 carbon atoms, or halogen; $n^1$ and $n^2$ are independently 0 or 1; $R^3$ is hydrogen, lower alkyl containing 1 to 3 carbon atoms, alkoxy containing 1 to 2 carbon atoms; R⁴ is lower alkyl containing 1 to 3 carbon atoms or alkoxy containing 1 to 2 carbon atoms, or the pharmaceutically acceptable salts thereof.

3. A compound according to claim 2 4-[1-(5-bromo-2-naphthalenyl)ethyl]-3H-1,2,3,5-oxathiadiazole 2-oxide or the pharmaceutically acceptable salts thereof.

4. A compound according to claim 2 4-[1-(3-methyl-2-naphthalenyl)-ethyl]-3H-1,2,3,5-oxathiadiazole 2-oxide or the pharmaceutically acceptable salts thereof.

5. A compound according to claim 2 4-[1-methyl-2-(2-naphthalenyl)-ethyl]-3H-1,2,3,5-oxathiadiazole 2-oxide or the pharmaceutically acceptable salts thereof.

6. A compound according to claim 2 4-[1-(2-naphthalenyl)ethyl]-3H-1,2,3,5-oxathiadiazole 2-oxide or the pharmaceutically acceptable salts thereof.

7. A compound according to claim 1 4-[(2-naphthalenylthio)methyl]-3H-1,2,3,5-oxathiadiazole 2-oxide or the pharmaceutically acceptable salts thereof.

8. A compound according to claim 2 4-[2-(2-naphthalenyl)propyl]-3H-1,2,3,5-oxathiadiazole 2-oxide or the pharmaceutically acceptable salts thereof.

9. A compound according to claim 2 4-[1-methyl-1-2-naphthalenyl)ethyl]-3H-1,2,3,5-oxathiadiazole 2-oxide or the pharmaceutically acceptable salts thereof.

10. A compound according to claim 1 4-[1-(2-naphthalenyl)-2-phenylethyl]-3H-1,2,3,5-oxathiadiazole 2-oxide or the pharmaceutically acceptable salts thereof.

11. A compound according to claim 2 4-[2-methoxy-2-(2-naphthalenyl)ethyl]-3H-1,2,3,5-oxathiadiazole 2-oxide or the pharmaceutically acceptable salts thereof.

12. A compound according to claim 1 4-[(2-naphthalenylsulfonyl)methyl]-3H-1,2,3,5-oxathiadiazole 2-oxide or the pharmaceutically acceptable salts thereof.

13. A compound according to claim 1 4-[(2-naphthalenyloxy)methyl]-3H-1,2,3,5-oxathiadiazole 2-oxide or the pharmaceutically acceptable salts thereof.

14. A compound according to claim 1 4-[2-(2-naphthalenyl)ethenyl]-3H-1,2,3,5-oxathiadiazole 2-oxide or the pharmaceutically acceptable salts thereof.

15. A method of treating non-insulin dependent diabetes mellitus in humans by administering an effective amount of the compound of structural formula (I).

16. A pharmaceutical composition useful for treating non-insulin dependent diabetes mellitus in humans comprising an effective amount of a compound of structural formula (I) and a pharmaceutically acceptable carrier.

* * * * *